(12) United States Patent
Shimizu et al.

(10) Patent No.: US 7,712,174 B2
(45) Date of Patent: May 11, 2010

(54) ROLLING DRIVING ACTUATOR AND POWER TOOTHBRUSH USING THE SAME

(75) Inventors: Hiroaki Shimizu, Hikone (JP); Ryo Motohashi, Hikone (JP); Hidekazu Yabuuchi, Hikone (JP); Takahiro Nishinaka, Omihachiman (JP); Katsuhiro Hirata, Sanda (JP); Yuya Hasegawa, Kyoto (JP)

(73) Assignee: Panasonic Electric Works Co., Ltd., Osaka (JP)

( * ) Notice: Subject to any disclaimer, the term of this patent is extended or adjusted under 35 U.S.C. 154(b) by 1066 days.

(21) Appl. No.: 10/557,055

(22) PCT Filed: May 14, 2004

(86) PCT No.: PCT/JP2004/006557

§ 371 (c)(1),
(2), (4) Date: Jan. 17, 2006

(87) PCT Pub. No.: WO2004/102776

PCT Pub. Date: Nov. 25, 2004

(65) Prior Publication Data

US 2007/0011834 A1 Jan. 18, 2007

(30) Foreign Application Priority Data

May 16, 2003 (JP) .............................. 2003-139572

(51) Int. Cl.
*A61C 17/22* (2006.01)
(52) U.S. Cl. ......................................... 15/22.1; 15/22.2
(58) Field of Classification Search ................. 15/22.1, 15/22.2, 23, 21.1, 28

See application file for complete search history.

(56) References Cited

U.S. PATENT DOCUMENTS

2002/0195884 A1 12/2002 Ichii et al.
2003/0110615 A1 6/2003 Ku et al.

(Continued)

FOREIGN PATENT DOCUMENTS

CN 2080343 7/1991

(Continued)

OTHER PUBLICATIONS

English language Abstract of DE 19816201, Oct. 15, 1998.

(Continued)

*Primary Examiner*—Shay L Karls
(74) *Attorney, Agent, or Firm*—Greenblum & Bernstein P.L.C.

(57) ABSTRACT

In a rolling driving actuator used as a drive source of a power toothbrush, permanent magnets are formed flat plate shape, and constituting a moving object by being attached to grooves formed on an outer peripheral face of a yoke which is press-fitted to and fixed on a shaft. On the other hand, a tubular shaped stator, which is constituted by a coil wound around a bobbin and stationary yokes provided on both side of the bobbin in axial direction of the shaft, is provided to face an outer face of the permanent magnet or an outer face of the yoke of the moving object with a predetermined clearance so that a center axis thereof becomes coaxial with the center axis of the shaft. By supplying an alternating current to the coil, the moving object is driven in rolling driving around the axis of the shaft.

16 Claims, 14 Drawing Sheets

U.S. PATENT DOCUMENTS

2005/0235438 A1    10/2005    Motohashi et al.
2006/0010622 A1    1/2006    Naruse et al.

FOREIGN PATENT DOCUMENTS

| | | |
|---|---|---|
| DE | 19816201 | 10/1998 |
| EP | 0221228 | 5/1987 |
| EP | 1193844 | 4/2002 |
| JP | 60-156711 | 10/1985 |
| JP | 62-104468 | 5/1987 |
| JP | 63-29604 | 2/1988 |
| JP | 63-125281 | 5/1988 |
| JP | 4-075457 | 3/1992 |
| JP | 9-173360 | 7/1997 |
| JP | 10-150755 | 6/1998 |
| JP | 10-248231 | 9/1998 |
| JP | 11-146625 | 5/1999 |
| JP | 2001-37192 | 2/2001 |
| JP | 2002-34224 | 1/2002 |
| JP | 2002-176758 | 6/2002 |
| WO | 02078154 | 10/2002 |

OTHER PUBLICATIONS

English language Abstract of JP 2001-37192, Feb. 9, 2001.
English language Abstract of JP 10-150755, Jun. 2, 1998.
English Language Abstract of JP 9-173360, Jul. 8, 1997.
English Language Abstract of JP 2002-176758, Jun. 21, 2002.
English Language Abstract of JP 4-075457, Mar. 10, 1992.
English Language Abstract of JP 62-104468, May 14, 1987.
U.S. Appl. No. 10/557,253 to Shimizu et al., filed Nov. 16, 2005.
U.S. Appl. No. 10/557,252 to Shimizu et al., filed Nov. 16, 2005.

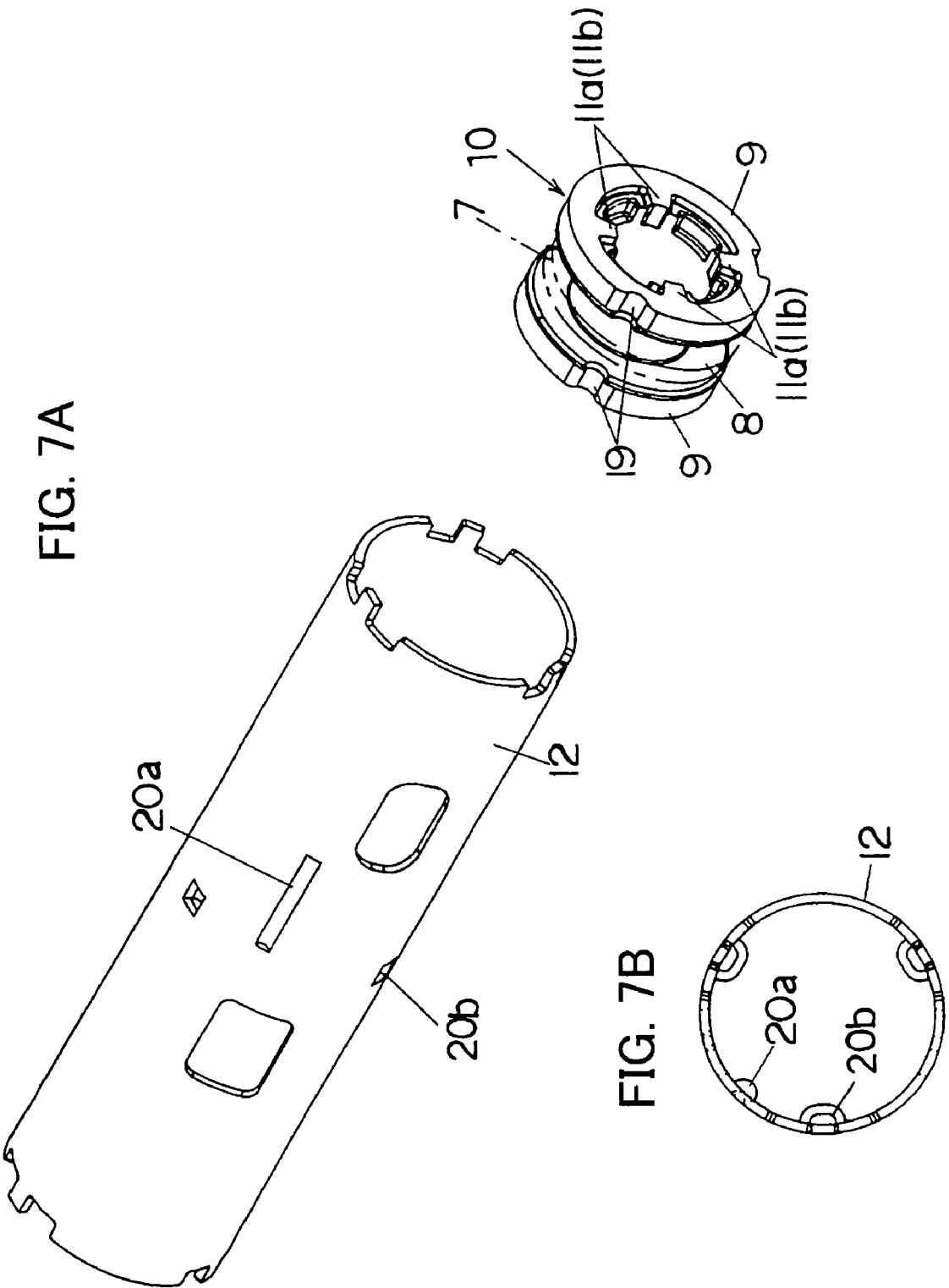

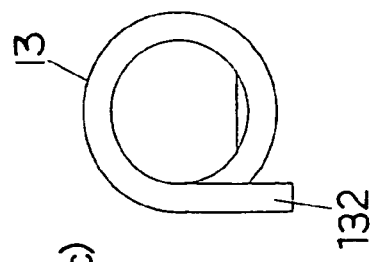
FIG. 8C
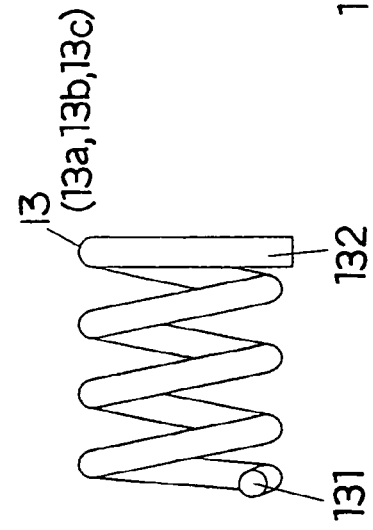
FIG. 8B
FIG. 8A
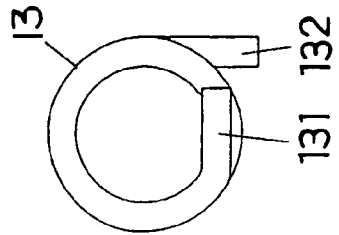
FIG. 9A
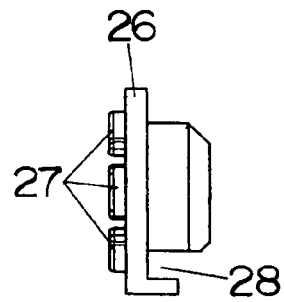
FIG. 9B
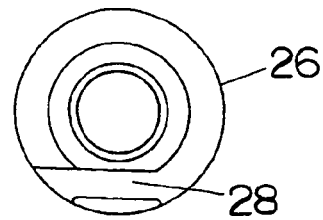

ROLLING DRIVING ACTUATOR AND POWER TOOTHBRUSH USING THE SAME

CONTINUING DATA

This application is a 371 of PCT/JP04/06557, filed May 14, 2004.

TECHNICAL FIELD

The present invention relates to a rolling driving actuator and a power toothbrush using the same.

BACKGROUND ART

As shown in, for example, Japanese Laid-Open Patent Application No. 9-173360, a power toothbrush, which can perform reciprocal linear driving in axial direction of a shaft and reciprocal rotation driving (rolling driving) around the axis selectively with using mechanical driving conversion mechanism, is known. In this power toothbrush, it is possible selectively to perform two motions of the reciprocal linear driving in the axial direction of the shaft and the rolling driving around the axis of the brush body attached to the shaft via the driving conversion mechanism by switching rotation direction of a motor.

In such a power toothbrush utilizing the mechanical driving conversion mechanism, a configuration of the driving conversion mechanism for switching between the reciprocal linear driving in the axial direction of the shaft and the rolling driving around the axis becomes complex. According to this, the power toothbrush becomes upsizing, and assembly of it becomes difficult causing the increase of the cost.

On the other hand, for example, Japanese Laid-Open Patent Publication No. 2002-176758 shows a power toothbrush which reciprocally and linearly drives a brush body attached on a shaft in axial direction of the shaft with using a reciprocation type linear driving actuator. This reciprocation type linear driving actuator can perform only the reciprocal linear driving of the shaft, but cannot perform the rolling driving. It, however, is described as a reference of the conventional actuator using permanent magnets and coil.

This conventional actuator is described with reference to FIG. 16. With this conventional reciprocation type linear driving actuator 150, a plunger 151 formed of a magnetic material is fixed on an outer periphery of a shaft 152. The shaft 152 is pivoted by a bearing 162 capable of reciprocally and linearly moving in a direction (axial direction) parallel to the center axis thereof. A ring shaped coil 154 is disposed on an inner peripheral surface of a shielding case 153 with a predetermined clearance with respect to the outer periphery of the plunger 151. Furthermore, ring shaped permanent magnets 155 and 156 which are magnetized in symmetrical with respect to the coil 154 are disposed on the inner peripheral surface of the shielding case 153 and on both sides of the coil 154 in the above axial direction. Ring shaped first yokes 157 and 158 are respectively disposed between the permanent magnets 155 and 156 and the coil 154, and ring shaped second yokes 159 and 160 are disposed at positions opposite to the permanent magnets 155 and 156 with respect to the coil 154. A spring member 161 is disposed between the plunger 151 and the shielding case 152 (SIC: correctly 153) for applying an accompanying force to the plunger 151 in a one direction among the reciprocation directions of linear driving. Then, by supplying an alternating current to the coil 154, the plunger 151 can be reciprocally and linearly driven in the axial direction.

However, in the above-mentioned reciprocation type linear drive actuator 150 using the conventional permanent magnets and the coil, the permanent magnets 155 and 156 are disposed with the clearance with respect to the outer periphery of the plunger, so that inside diameter and outside diameter of the ring shaped permanent magnets 155 and 156 become larger, and volumes of the permanent magnets 155 and 156 also become larger. Following to this, the cost of the permanent magnets 155 and 156 in material becomes expensive. Furthermore, since the permanent magnets 155 and 156 are formed as the ring shape by combination of a plurality of arc-shaped permanent magnets, manufacturing process of the ring shaped permanent magnets 155 and 156 becomes complicated, and the cost of them in manufacturing becomes expensive. As a result, the costs of the actuator using the conventional permanent magnets and coil and the power toothbrush using the same become expensive. Still furthermore, since the permanent magnets 155 and 156 are larger, it is difficult to realize the miniaturization and weight saving of the actuator 150 and the power toothbrush using the same.

DISCLOSURE OF THE INVENTION

The present invention is done to solve the problems of the above-mentioned conventional ones and purposed to provide a rolling driving actuator enabling low cost, miniaturization, weight saving and improvement of assemble workability, and to provide a power toothbrush using the same with low cost, miniaturization and weight saving.

For achieving the above mentioned purpose, a rolling driving actuator in accordance with an aspect of the present invention comprises: a moving object having a shaft pivoted to be able to rotate around an axis thereof, a yoke fixed on the shaft and at least one flat plate shaped permanent magnet attached to adjoin the yoke around the axis of the shaft and magnetized in thickness direction thereof; and a tubular shaped stator having a coil wound around the axis of the shaft to enclose the moving object, and stationary yokes made of a magnetic material and disposed to face an outermost peripheral portion of the yoke and the permanent magnet with a predetermined clearance in a direction perpendicular to the axis of the shaft; and the moving object is driven in rolling driving in a predetermined angle region around the axis of the shaft by supplying alternating current to the coil.

Furthermore, a power toothbrush in accordance with an aspect of the present invention comprises: a brush body that brush is implanted at a front end thereof; a rolling driving actuator for rolling driving the brush body in a predetermined direction; an electric power supply for supplying electric power to the rolling driving actuator; and a driving circuit for supplying driving current to the rolling driving actuator. The rolling driving actuator comprises: a moving object having a shaft pivoted to be able to rotate around an axis thereof, a yoke fixed on the shaft and at least one flat plate shaped permanent magnet attached to adjoin the yoke around the axis of the shaft and magnetized in thickness direction thereof; and a tubular shaped stator having a coil wound around the axis of the shaft to enclose the moving object, and stationary yokes made of a magnetic material and disposed to face an outermost peripheral portion of the yoke and the permanent magnet with a predetermined clearance in a direction perpendicular to the axis of the shaft; and the moving object is driven in rolling driving in a predetermined angle region around the axis of the shaft by supplying alternating current to the coil.

In this way, since the flat plate shaped permanent magnet is attached to the shaft of the moving object, a volume of the permanent magnet becomes smaller in comparison with the case that the permanent magnet is provided on the stator side like the conventional one, and a cost of the permanent magnet in material can be reduced. Furthermore, since the permanent magnet is magnetized in the thickness direction, manufacturing process of the permanent magnet becomes simple, and thereby the cost of the permanent magnet in manufacture can be reduced. Still furthermore, polarities on an outer face of the permanent magnet and on an outer face of the yoke becomes opposite to each other, so that magnetic flux by the permanent magnet can easily be passed through the yoke, and the magnetic flux by the permanent magnet can be utilized efficiently. Still furthermore, assemble workability of the rolling driving actuator is improved and it can be miniaturized and lightweighted in comparison with conventional one using the mechanical drive converting mechanism. Consequently, the rolling driving actuator of low cost, miniaturized and lightweighted and the power toothbrush using the same can be provided.

BRIEF DESCRIPTION OF THE DRAWINGS

FIG. 7A is an exploded perspective view showing a configuration of a shielding case and the moving object of the above rolling driving actuator. FIG. 7B is a sectional front view showing the configuration of the above shielding case.

FIGS. 8A to 8C are respectively a front view, a side view and a rear view showing a configuration of a spring member of the above rolling driving actuator.

FIGS. 9A and 9B are respectively a side view and a front view showing a configuration of a spring receiving member of the above rolling driving actuator.

BEST MODE FOR CARRYING OUT THE INVENTION

A rolling driving actuator and a power toothbrush using the same in accordance with an embodiment of the present invention are described with reference to drawings.

Figure 1:
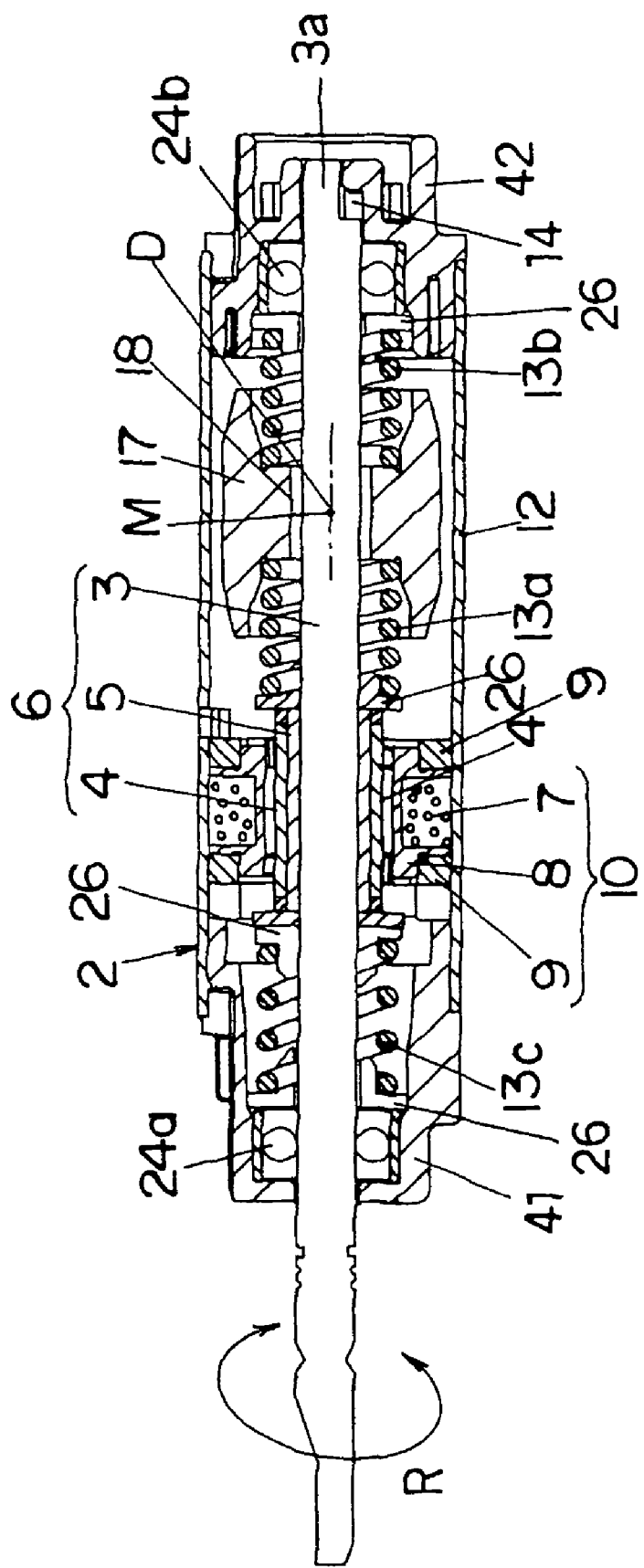
FIG. 1 is a sectional view showing a configuration of a rolling driving actuator in accordance with an embodiment of the present invention.
Figure 2:
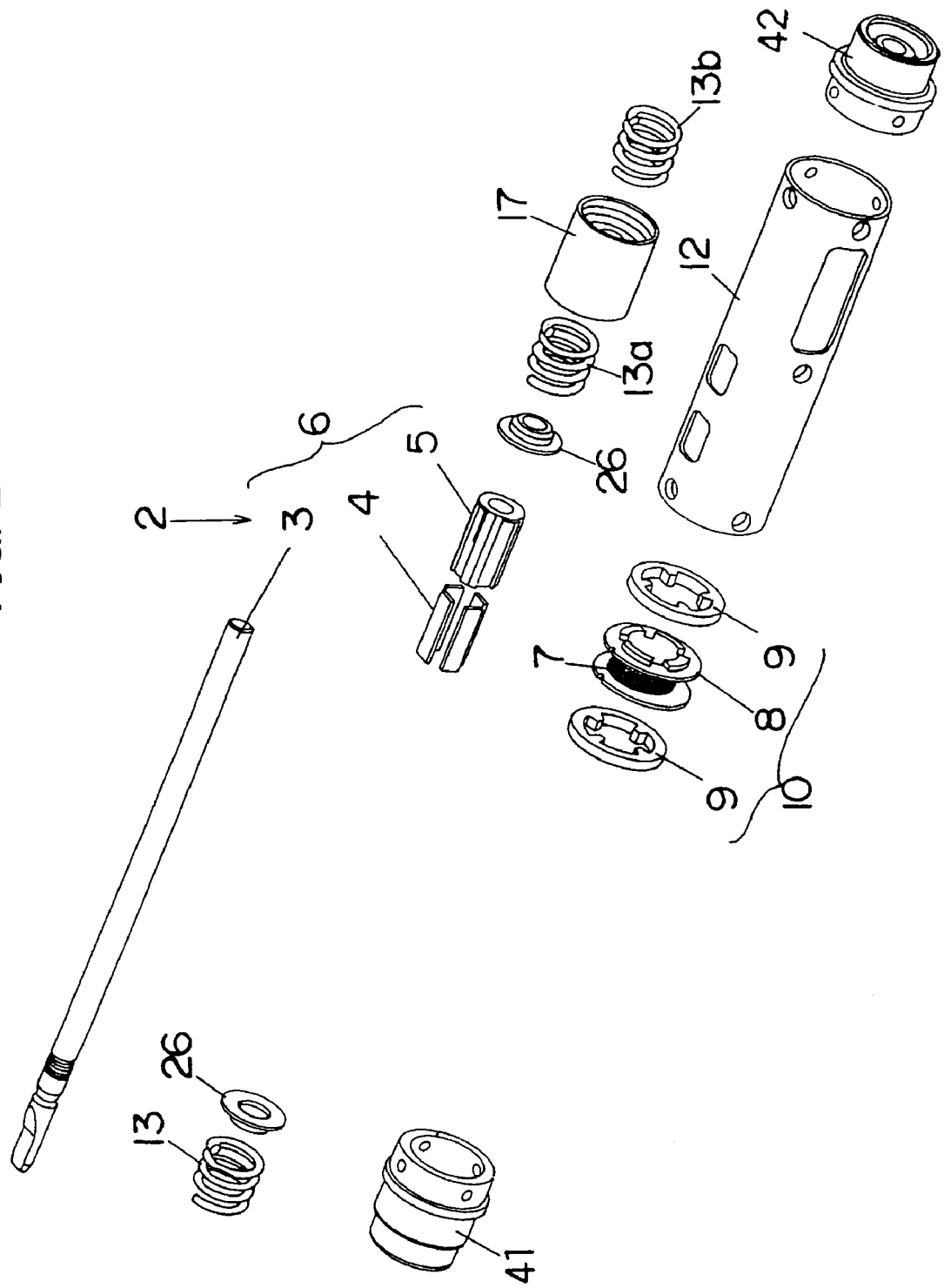
FIG. 2 (SIC) is a view showing a structure for restricting rotation angle of a shaft which is provided at a rear end portion of the rolling driving actuator shown in FIG. 1.
Figure 3:
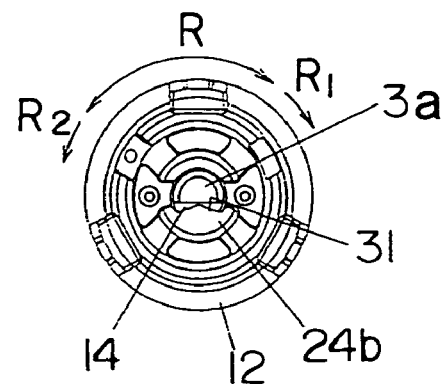
FIG. 3 (SIC) is an exploded perspective view of the rolling driving actuator shown in FIG. 1.

First, the rolling driving actuator in accordance with this embodiment which is suitable for an actuator of the power toothbrush is described. FIG. 1 is a sectional side view showing a configuration of the rolling driving actuator 2 in accordance with this embodiment. FIG. 2 is an exploded perspective view of the rolling driving actuator 2. FIG. 3 is a view showing a structure for restricting rotation angle of a shaft which is provided at a rear end portion of the rolling driving actuator shown in FIG. 1.

As shown in FIG. 1 and FIG. 2, a shielding case 12 is a substantially cylindrical shape, and sealing members 41 and 42 are respectively fitted and fixed to front and rear openings thereof. Furthermore, bearings 24a and 24b for pivoting a shaft 3 reciprocally and rotatably around an axis thereof in a predetermined region as shown by arrow R are respectively provided on the sealing members 41 and 42.

A moving object 6 is configured by the shaft 3, a yoke 5 press-fitted to and fixed on the shaft 3, a flat plate shaped permanent magnets 4 fixed on the yoke 5, and so on. In this embodiment, the shaft 3 is made of a nonmagnetic material. By making the shaft 3 of the nonmagnetic material, no magnetic flux leaks through the shaft 3, so that power loss can be reduced. Beside, the nonmagnetic material is generally expensive. And, strength of inexpensive nonmagnetic material is lower. Thus, when leakage of magnetic flux through the shaft 3 can be permitted a little, the shaft 3 may be made of magnetic material to increase the strength.

A stator 10 is configured by a bobbin 8, a coil 7 constituted by winding a wire around the bobbin 8, stationary yokes 9 disposed at both sides of the bobbin 8 in axial direction of the shaft 3, and so on. The stator 10 is formed substantially tubular shape, and fixed on an inner peripheral face of the shielding case 12. When the shaft 3 is pivoted by the bearings 24a and 24b, the moving object 6 is held in a manner so that an outermost peripheral portion of the moving object 6 in a direction perpendicular to the axis of the shaft 3 keeps a predetermined clearance with respect to an innermost peripheral portion of the stator 10. In this way, by rotatably inserting the moving object 6 into the inside of the stator 10, a magnetic path of the rolling driving actuator 2 is constituted.

In the axial direction of the shaft 3, ring shaped spring receiving members 26 made of a nonmagnetic material are respectively attached to both side of the yoke 5. Furthermore, the same spring receiving members 26 are respectively attached to a rear face of the bearing 24a in front side and a front face of the bearing 24b in rear side. Still furthermore, a vibrational absorption spindle 17 of a substantially cylindrical shape is engaged with the shaft 3 between the moving object 6 and the bearing 24b in rear side with a relatively large tolerance. Then, coil springs (SIC) 13a and 13b are respectively provided between the spring receiving members 26 and the vibrational absorption spindle 17, and a coil spring (SIC) 13c is provided between the spring receiving member 26 of the moving object 6 and that of the bearing 24a in front side.

Figure 10:
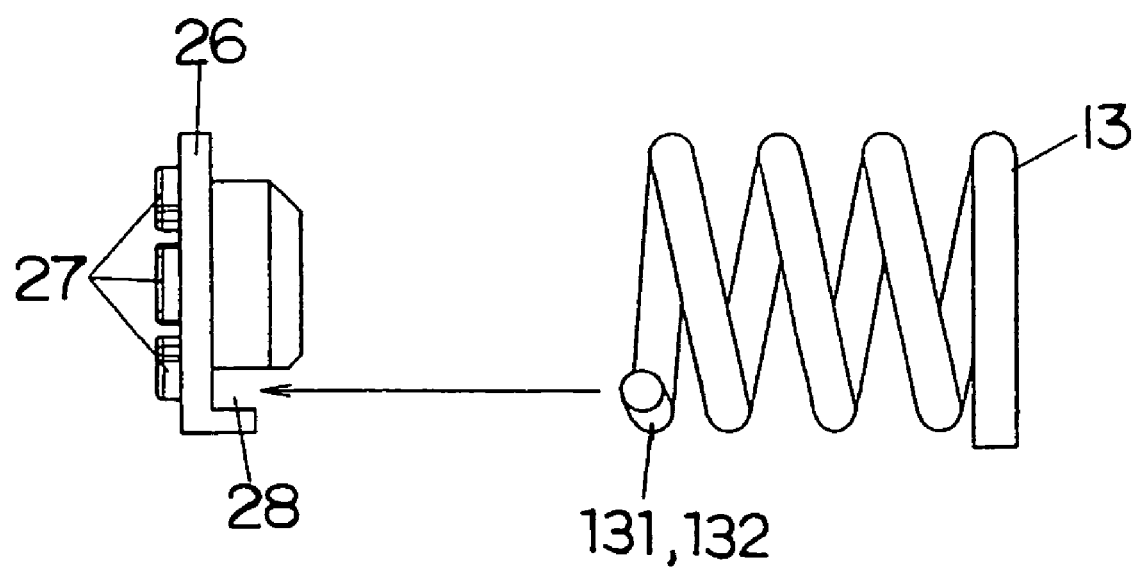
FIG. 10 is a side view showing a state that an end of the spring member is engaged with the above spring receiving member.
Figure 11C:
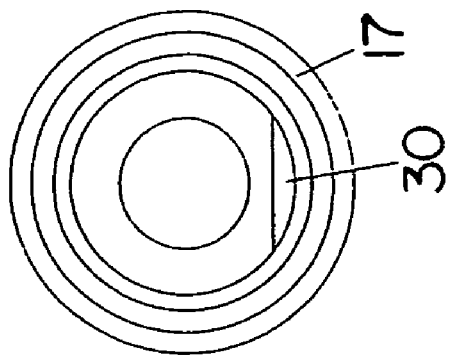
FIGS. 11A to 11D are respectively a front view, a sectional side view, a rear view and a perspective view showing a vibrational absorption spindle of the above rolling driving actuator.
Figure 11D:
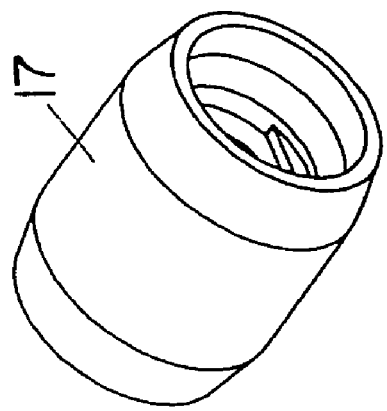
Figure 11B:
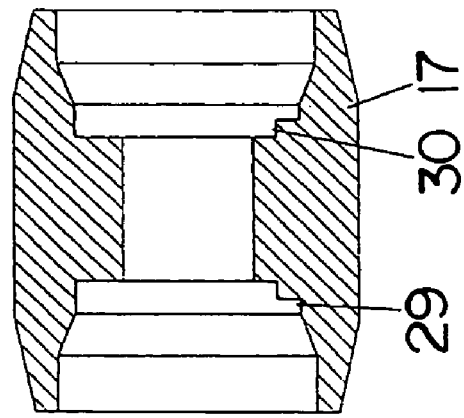
Figure 11A:
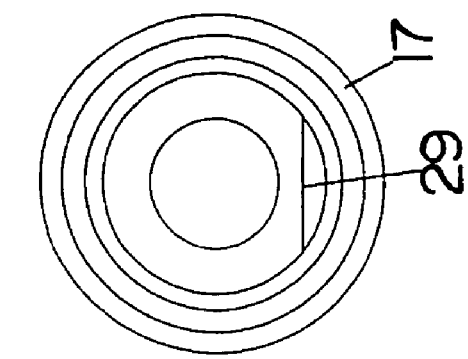

A configuration of the spring members 13a, 13b and 13c is shown in FIGS. 8A to 8C. Furthermore, a configuration of the spring receiving member 26 is shown in FIGS. 9A and 9B. Still furthermore, a coupling structure of each of the spring members 13a, 13b and 13c and the spring receiving member 26 is shown in FIG. 10. As shown in FIGS. 8A to 8C, each of the spring members 13a, 13b and 13c is substantially the same shape and constituted by a torsion coil spring 13 having two arms 131 and 132. As shown in FIGS. 9A and 9B, a hooking portion 28 is formed on each spring receiving member 26 to nip the arm 131 or 132 of each spring member 13a, 13b and 13c for restricting rotation of the spring members 13a, 13b and 13c.

Furthermore, a configuration of the vibrational absorption spindle 17 is shown in FIGS. 11A to 11D. As shown in FIGS. 11A to 11D, hooking portions 29 and 30 are formed on the vibrational absorption spindle 17 for preventing the rotation by hooking the arm 131 or 132 of the spring members 13a and 13b. In this way, since respective arms 131 and 132 of three spring members 13a, 13b and 13c are fixed for stopping the rotation by the hooking portions 28, 29 and 30 of the spring receiving members 26 and the vibrational absorption spindle 17, the moving object 6 is held in a state of rotatable around the axis of the shaft 3 shown by arrow R, and elastic forces are charged in respective spring members 13a, 13b and 13c corresponding to rotation motion of the moving object 6 around the axis of the shaft 3. As a result, an angular region where the moving object 6 is rotatable around the axis of the shaft 3 is restricted, so that rolling angle of the shaft 3 is decided.

By the way, in the above structure for restricting the rotation of the moving object 6 by only the spring members 13a, 13b and 13c, there is a possibility that the moving object 6 rotates over a permissible region when a force for rotating the moving object 6 more than the permissible region around the axis of the shaft 3 from outside, so that it may affect driving characteristic of the actuator. Thus, a rotation restricting structure of the shaft 3 shown in FIG. 3 is provided for mechanically stopping the rotation of the moving object 6 when a rotation force more than the permissible region is applied to the moving object 6 around the axis of the shaft from outside.

A rear end portion 3a of the shaft 3 is formed to have a substantially D-shaped section. On the other hand, a substantially sector shaped fitting hole 14 into which the rear end portion 3a of the shaft 3 is fitted thereby restricting the rotation of the shaft 3 around the axis is formed on the sealing member 42 in rear side. By fitting the rear end portion 3a of the shaft 3 into the fitting hole 14, rotation angle around the axis of the shaft 1 (SIC) is restricted in a fixed region. Although tapered faces 31 are formed to be a angle section on the fitting hole 14, when the moving object 6 is in a neutral position of amplitude, a flat face portion of substantially D-shaped section of the rear end portion 3a of the shaft 3 does not contact with the tapered faces 31 of angle section, so that the moving object 6 is reciprocally rotatable around the axis of the shaft 3. When the moving object 6 rotates over the permissible region around the axis of the shaft 3 in a direction shown by arrow R1, the flat face portion of substantially D-shaped section of the rear end portion 3a of the shaft 3 contacts with the tapered faces 31 of angle section, so that the rotation is restricted more. The same goes for the case for rotating in opposite direction shown by arrow R2. Thereby, the rotation of the moving object 6 over the rolling angle is mechanically restricted, so that reliability of the rolling driving actuator 2 against the externally applied load or impact load, and so on can be ensured.

In addition, the rear end portion 3a of the shaft 3 is used as a reference plane when the yoke 5 is press-fitted to and fixed on the shaft 3, too. Specifically, by press-fitting the yoke 5 in a manner so that a flat bottom face 25a of a rectangular cornered U-shaped groove 25 of the yoke 5 (refer to FIG. 4) and the flat face portion of substantially D-shaped section of the rear end portion 3a of the shaft 3 become substantially parallel to each other, a proper assembling angle of the yoke 5 with respect to the shaft 3 can easily be defined.

Figure 4:
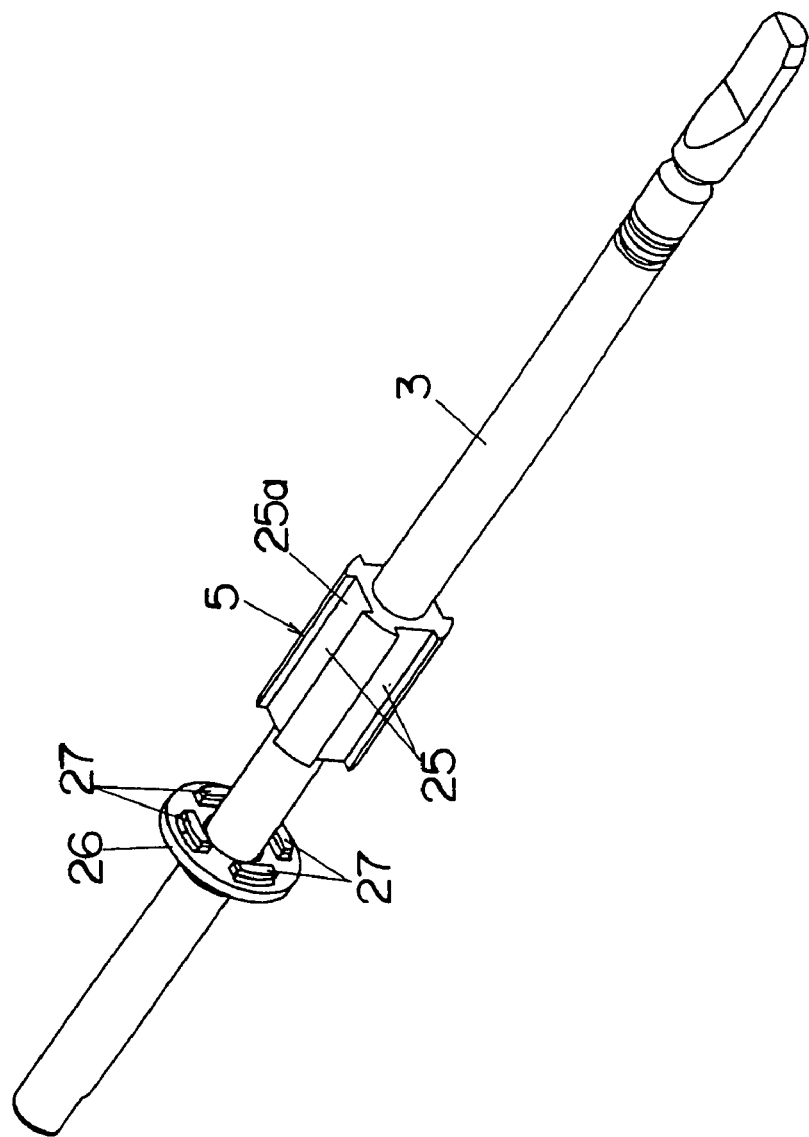
FIG. 4 is a perspective view showing a state that a yoke and spring receiving members are assembled on the shaft constituting a moving member of the above rolling driving actuator.
Figure 5C:
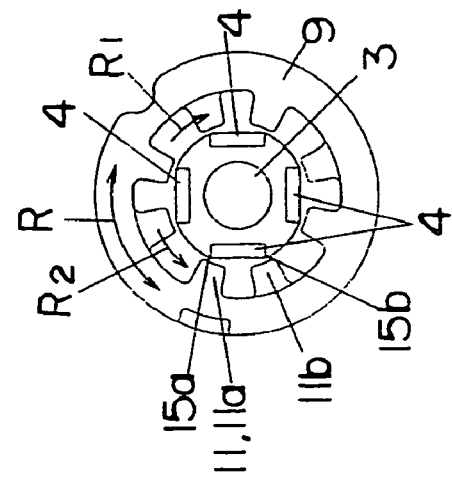
FIG. 5C is a front view showing the configuration of the above opposing portion of the moving object and the stator.
Figure 5A:
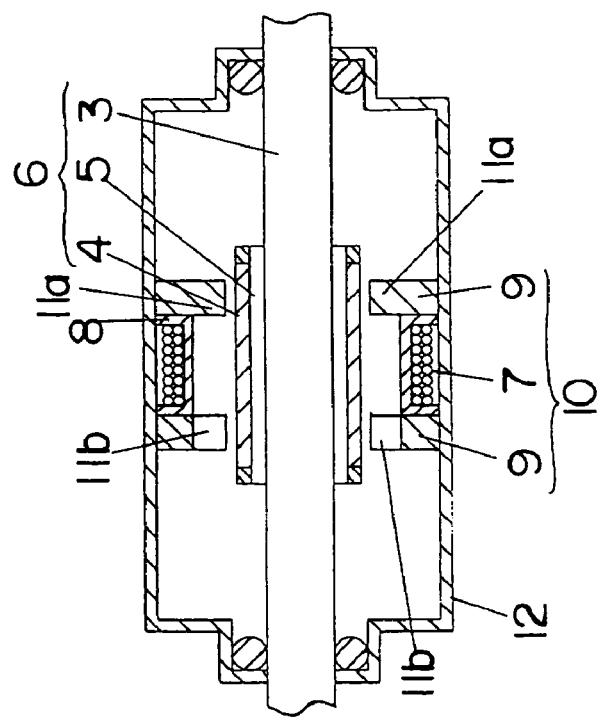
FIG. 5A is a sectional side view showing a configuration of an opposing portion of the moving object and a stator of the above rolling driving actuator.
Figure 5B:
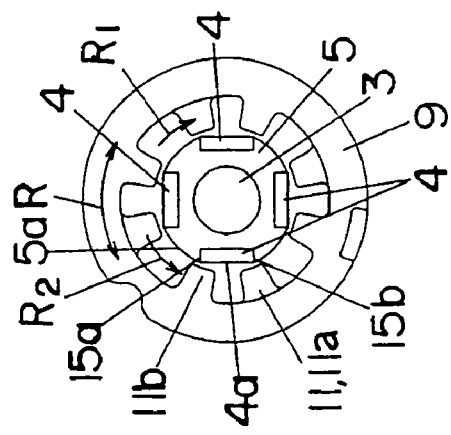
FIG. 5B is a rear view showing the configuration of the above opposing portion of the moving object and the stator.

A state that the yoke 5 is press-fitted to and fixed on the shaft 3 is shown in FIG. 4. Furthermore, a configuration of an opposing portion of the moving object 6 and the stator 10, that is, a main portion for generating driving force is shown in FIG. 5A to FIG. 5C. As can be seen from these figures, the yoke 5 is formed of a magnetic material to be substantially tubular shape, and at least one (four in the figures) of groove 25 is formed on an outer peripheral face thereof. Each groove 25 is formed along the axis of the shaft 3 to have a substantially U-shaped section (channel shape) so that a bottom face thereof is to be flat. Then, since a depth of the groove 25 and a thickness of the permanent magnet 4 and a width of the groove 25 and a width of the permanent magnet 4 are respectively set to be substantially equal, the flat plate shaped permanent magnets 4 are respectively fitted to the grooves 25 substantially with no clearance, as shown in FIG. 5A to FIG. 5C. As a result, it becomes a state that an outer face 4a of each flat plate shaped permanent magnet 4 is disposed to adjoining an arc shaped outer face 5a of the yoke 5.

Each permanent magnet 4 is magnetized in thickness direction so that a polarity of the outer face 4a and a polarity of an inner face 4b in a direction perpendicular to the axis of the shaft 3 are different from each other. Furthermore, each permanent magnet 4 is fixed on the yoke 5 in the same orientation that, for example, all of the outer faces 4a of four permanent magnets 4 become N-pole. By fixing the permanent magnets 4 on the yoke 5 in this way, all arc shaped outer faces 5a of the yoke 5 disposed between two adjoining permanent magnets 4 become S-pole, and vice versa.

FIGS. 5A to 5C respectively show an initial state that no current is supplied to the coil 7. When no current is supplied to the coil 7, the moving object 6 is stopped at a position where the magnetic force of the permanent magnets 4 applied to the stationary yokes 9 and forces of the spring members 13 are balanced. Then, magnetic poles 11a and 11b provided on the stationary yokes 9 are respectively positioned to face the permanent magnets 4. When a unidirectional current is supplied to the coil 7, the magnetic poles 11a of one stationary yoke 9 become N-pole, and the magnetic poles 11b of the other stationary yoke 9 become S-pole. Thus, as shown in FIG. 3, the moving object 6 rotates in a direction around the axis, for example, in the direction shown by arrow R1. When a reverse current is supplied to the coil 7, the magnetic poles 11a of one stationary yoke 9 become S-pole, and the magnetic poles 11b of the other stationary yoke 9 become N-pole. Thus, the moving object 6 rotates in the other direction around the axis, for example, in the direction shown by arrow R2. Accordingly, by supplying an alternating current to the coil 7, it is possible to perform the rolling driving of the moving object 6 in a predetermined angle region around the axis of the shaft 3 as shown by arrow R.

In this way, a vibration system of the rolling driving is constituted by the moving object 6 which performs the rolling driving in a predetermined angle region around the axis of the shaft 3 and the spring members 13 for supporting the moving object 6 around the axis. The spring member 13 is tortured in tightening direction and in loosening direction corresponding to the rolling driving around the axis of the moving object 6. As a result, it applies a charging force in a direction for restricting the rotation around the axis of the moving object 6. By applying a current having a frequency near to a resonance vibration frequency defined by a spring constant of the spring members 13 and a mass of the moving object 6 to the coil 7, oscillation quantity (amplitude quantity) of the moving object 6 can be enlarged.

In addition, as shown in FIG. 4, since a plurality of protrusions 27 is provided on a face of the spring receiving member 26, when the protrusions 27 are inserted into end portions of the grooves 25 of the yoke 5 in longitudinal direction, the spring receiving members 26 are fixed to the yoke 5 nonrotatably.

Figure 6:
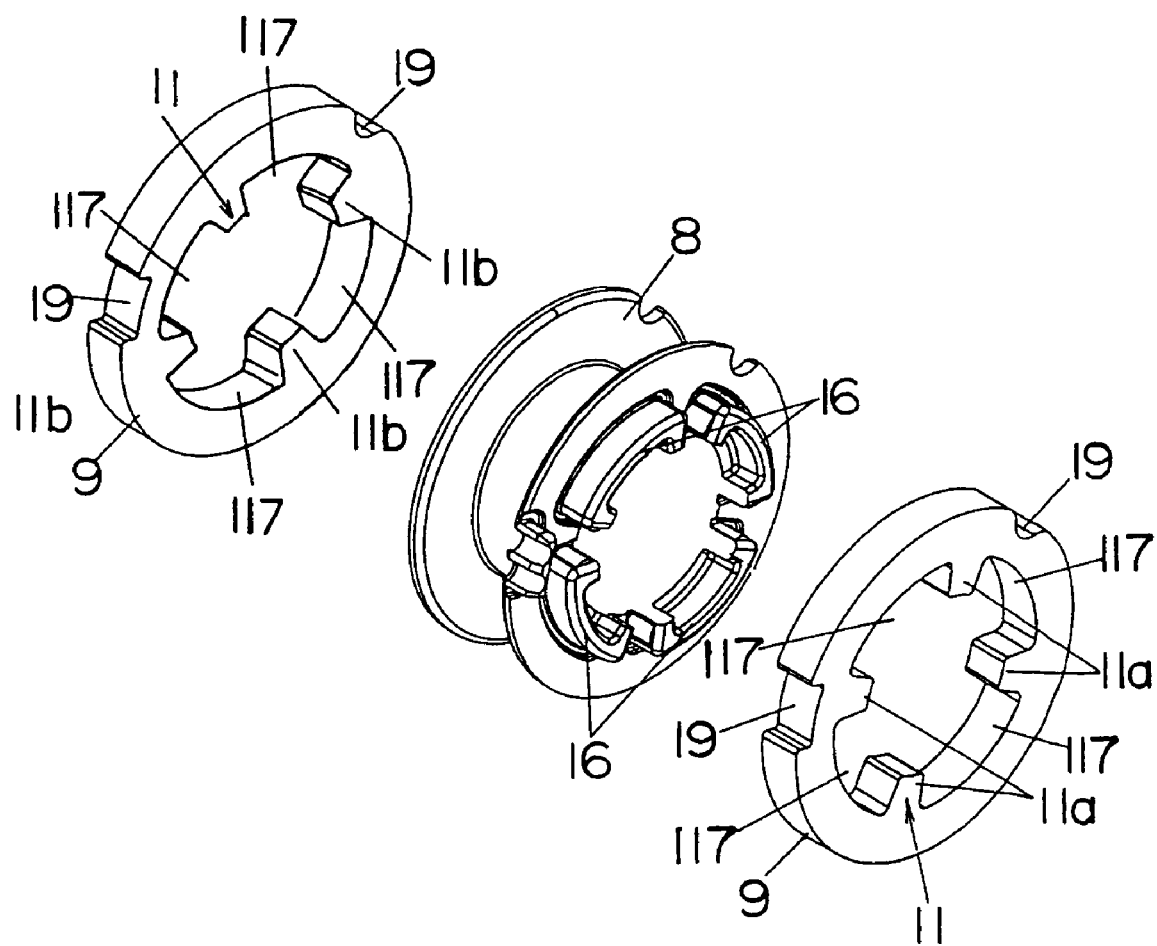
FIG. 6 is an exploded perspective view showing a configuration of a bobbin and stationary yokes constituting the stator of the above rolling driving actuator.

As shown in FIG. 5B and FIG. 5C, a number of magnetic poles 11 less than a predetermined number (four positions in the figure) is provided on an inner periphery portion of each stationary yoke 9 for facing poles of the moving object 6 (the outer faces 4a of the permanent magnets 4 and outer faces 5a of the yoke 5). As shown in FIG. 6, cuttings 117 are respectively formed between adjoining two magnetic poles 11 of the stationary yoke 9. In this way, by providing the cuttings 117 between the magnetic poles 11, it is possible to reduce leakage of magnetic flux to the shaft 3 even when the shaft 3 is made of a magnetic material such as iron, so that the magnetic flux by the permanent magnets 4 can be utilized effectively in the stationary yokes 9 side. Beside, it is sufficient that the number of the magnetic poles 11 is more than at lest one, but it is possible to increase the number of the magnetic poles 11 to the same number as the number (four) of the permanent magnets 4.

In case of providing the stationary yokes 9 on both sides of the bobbin 8 in the axial direction of the shaft 3 shown in FIG. 5A, the stationary yokes 9 are respectively disposed in a manner so that positions of the magnetic poles 11a of one stationary yoke 9 are not coincided with positions of the magnetic poles 11b of the other stationary yoke 9 around the axis of the shaft 3 of the moving object 6, as shown in FIG. 5B and FIG. 5C. Furthermore, at the initial position of the moving object 6 when no current is supplied to the coil 7, each magnetic pole 11a of one stationary yoke 9 is positioned to face a contact point 15a of an end portion of the permanent magnet 4 and the yoke 5 around the axis of the shaft 3, and each magnetic pole 11b of the other stationary yoke 9 is positioned to face another contact point 15b of the other end portion of the same permanent magnet 4 and the yoke 5. Thereby, a gap of the magnetic pole 11a of one stationary yoke 9 and a gap of the magnetic pole 11b of the other stationary yoke 9 with respect to the same permanent magnet 4 becomes substantially the same, so that the rolling driving of the moving object 6 is effectively performed.

When a unidirectional current is supplied to the coil 7, the permanent magnet 4 receives magnetic repulsion force from the magnetic pole 11a of one stationary yoke 9 and simultaneously receives magnetic attraction force from the magnetic pole 11b of the other stationary yoke 9. Thus, the moving object 6 is rotatively driven in a direction around the axis of the shaft 3 (for, example, in a direction shown by arrow R1) with a large force. When a reverse current is supplied to the coil 7, the permanent magnet 4 receives magnetic attraction force from the magnetic pole 11a of one stationary yoke 9 and simultaneously receives magnetic repulsion force from the magnetic pole 11b of the other stationary yoke 9, so that the moving object 6 is rotatively driven in the other direction around the axis of the shaft 3 (for, example, in a direction shown by arrow R2) with a large force. Therefore, by supplying an alternating current to the coil 7, the rolling driving of the moving object 6 around the axis of the shaft 3 can be performed.

Furthermore, the outer face 4a of the permanent magnet 4 and the outer face 5a of the yoke 5, polarities of which are different from each other, are disposed to adjoin each other in a peripheral direction of the moving object 6, so that driving force for rotating the moving object 6 is generated between the magnetic poles 11a and 11b and the outer face 5s of the yoke 5. Still furthermore, the outer face 4a of the permanent magnet 4 is flat, so that an opposing area of it with respect to the magnetic pole 11 can be ensured largely. On the other hand, the outer face 5a of the yoke 5 is arc shape, so that a clearance between the magnetic pole 11 and it can be reduced with ensuring an opposing area of it with respect to the magnetic pole 11. Thus, the driving force for rotating the moving object 6 around the axis of the shaft 3 is further increased, and the driving force in an initial state of rotation of the moving object 6 becomes larger, so that the rolling driving can be started smoothly.

As shown in FIG. 6, stationary yoke positioning portions 16 for positioning the stationary yoke 9 with respect to the bobbin 8 are respectively provided on both end faces of the bobbin 8 in the axial direction of the shaft 3. In the example shown in FIG. 6, the stationary yoke positioning portions 16 each which is a protruding rib having an arc shape are provided for protruding at four positions with a predetermined distance. On the other hand, the cuttings 117 are formed between adjoining two magnetic poles 11 on the stationary yoke 9, as mentioned before. By attaching two stationary yokes 9 respectively on both end faces of the bobbin 8 along the axial direction of the shaft 3 in a manner so that the stationary yoke positioning portions 16 are respectively fitted into the cuttings 117 of the stationary yokes 9, the relative positions of two stationary yokes 9 around the axis of the shaft 3 are fixed.

Furthermore, as shown in FIG. 7, a rotation restricting portion 20a, which is protruded toward an inner peripheral face side by, for example, press work, is formed on the substantially cylindrical shaped shielding case 12. Corresponding to this, engaging concave portions 19 which are to be engaged with the rotation restricting portion 20a, are formed on the outer peripheral faces of the bobbin 8 and the stationary yokes 9. By fitting the stator 10 to the inner peripheral face of the shielding case 12 in a manner so that the engaging concave portions 19 are engaged with the rotation restricting portion 20a, the rotation of the stationary yokes 9 with respect to the shielding case 12 around the axis of the shaft 3 is restricted, too. Similarly, a plurality of stoppers 20b protruding toward the inner peripheral face side by, for example, press work is formed on the shielding case 12. For example, in FIG. 7A, when the stator 10 is going to be fitted to the inner peripheral face of the shielding case 12, for example, from an opening at right side of the shielding case 12, the stationary yoke 9 at left side contacts the stoppers 20b, so that the movement in the axial direction of the shaft 3 is restricted at that position. According to such a configuration, fixing operation of the stator 10 to the shielding case 12 becomes easier. Alternatively, by forming an engaging protruding portion on an outer peripheral face of each stationary yoke 9 and forming a concave groove on the inner peripheral face of the shielding case 12 by punching of press work as the rotation restricting portion 20a, substantially the same effect can be obtained.

As mentioned before, the vibrational absorption spindle 17 is provided in the vibration system of the rolling driving. The vibrational absorption spindle 17 has a substantially tubular shape, is disposed between the moving object 6 and the bearing portion 24b, and held in the axial direction of the shaft 3 by the spring members 13a and 13b. Since the position M of the center of gravity of the vibrational absorption spindle 17 is coaxially disposed on the same rotation axis D of the moving object 6.

In this embodiment, the stator 10 and the shielding case 12 are assumed stationary portion, and it can be handled as a system of two mass point vibration model of mass of the moving object 6 and mass of the vibrational absorption spindle 17. In this case, there are the first (low-order side) oscillation mode that moving object 6 and the vibrational absorption spindle 17 are driven in the same phase and the second (high-order side) oscillation mode that the moving object 6 and the vibrational absorption spindle 17 are driven in opposite phase. When the moving object 6 is performed the rolling driving around the axis of the shaft 3 of the moving object 6 by supplying a current having a frequency near to natural vibration frequency in the second vibration mode to the coil 7, the vibrational absorption spindle 17 which is driven in opposite phase cancels inertial force of the moving object 6. Thereby, the vibration propagated to the shielding case 12 can be reduced.

Furthermore, moment of inertia of the vibrational absorption spindle 17 is set to be larger than moment of inertia of the moving object 6 in rotation of the moving object 6. In this embodiment, the moment of inertia of the vibrational absorption spindle 17 is made larger than the moment of inertia of the moving object 6 by adjusting the weight of the vibrational absorption spindle 17. By increasing the moment of inertia of the vibrational absorption spindle 17, assisting force of the rotation of the moving object 6 is increased, so that the output power of the rolling driving actuator 2 is further increased. Still furthermore, the vibrational absorption spindle 17 is rotated in opposite phase to that of the moving object 6 around the axis of the shaft 3, so that it serves for increasing the output power by assisting the rotation of the moving object 6. Still furthermore, a gap 18 is provided between the vibrational absorption spindle 17 and the moving object 6 in a direction perpendicular to the axis of the shaft 3. The gap 18 is an air gap and serves to rotate the vibrational absorption spindle 17 around the axis of the shaft 3 with smooth motion and with no resistance. Although, it is possible to intervene a bearing or the like, it is preferable to provide the gap 18 for restricting the cost lower.

As mentioned above, in constitution of the rolling driving actuator 2, the flat plate shaped permanent magnets 4 are used, and the permanent magnets 4 are provided on the moving object 6 side instead of the stator 10 side, so that the volume of each permanent magnet 4 can be much smaller in comparison with the conventional case that tubular shaped permanent magnets are disposed on the inner face of the shielding case 12. As a result, it is possible to decrease the weight of the permanent magnet 4 in material corresponding to the miniaturization of the permanent magnet 4 and to reduce the cost thereof. Furthermore, the permanent magnet 4 can be manufactured by cutting a large plate shaped permanent magnet which is magnetized in thickness direction into a predetermined size, so that the manufacture of the permanent magnet becomes easier and the cost in manufacture can be reduced. Still furthermore, the flat plate shaped permanent magnets 4 magnetized in thickness direction are only fitted to the flat bottom face 25a of the substantially U-shaped groove 25 of the yoke 5, so that the assemble workability is improved. As a result, the cost of the rolling driving actuator 2 can be reduced. Still furthermore, the polarities of the outer faces 4a of the permanent magnets 4 and the outer faces 5a of the yoke 5 are alternatively reversed, so that the magnetic flux by the permanent magnets 4 can easily be passed through the yoke 5, and the magnetic flux by the permanent magnets 4 can be utilized effectively. Therefore, the driving efficiency of the rolling driving actuator 2 can be increased in comparison with the conventional one utilizing the mechanical drive conversion mechanism.

Subsequently, modified examples of the rolling driving actuator in accordance with the present invention are described. In the above description, two stationary yokes 9 are respectively provided on both sides of the bobbin in the axial direction of the shaft 3. It is possible to provide it only one side of the bobbin 8 in the axial direction of the shaft 3 as shown in FIGS. 12A and 12B or FIGS. 13A and 13B.

Figure 12A:
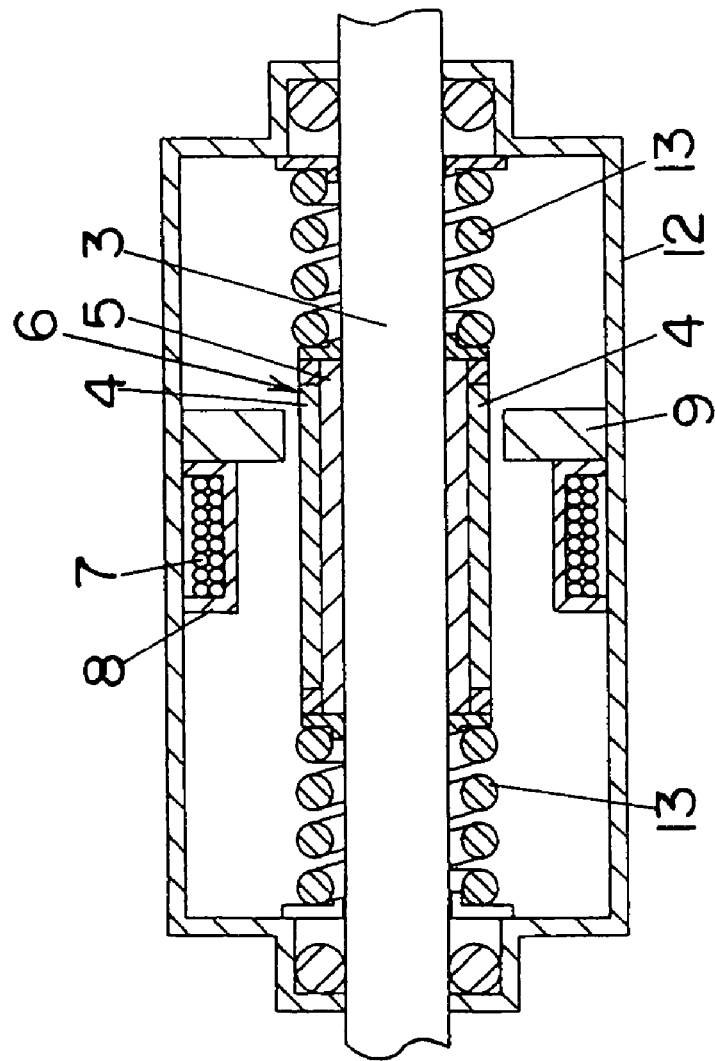
FIGS. 12A and 12B are respectively a sectional side view and a sectional rear view showing a modified example of the rolling driving actuator in accordance with the embodiment of the present invention.
Figure 12B:
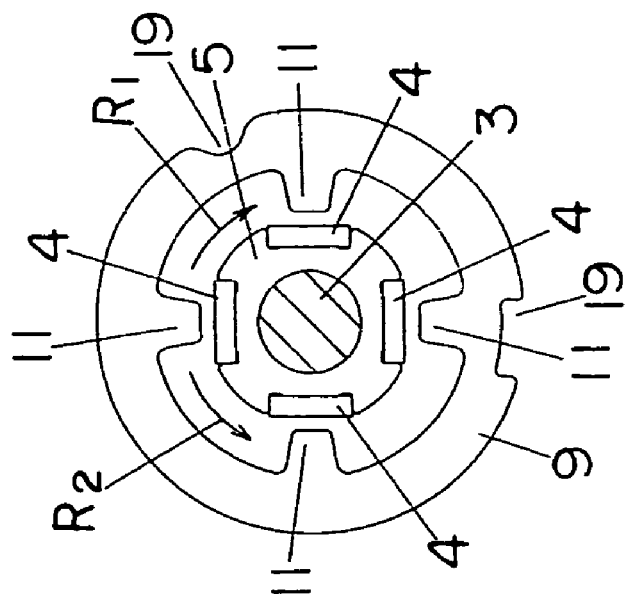
Figure 13A:
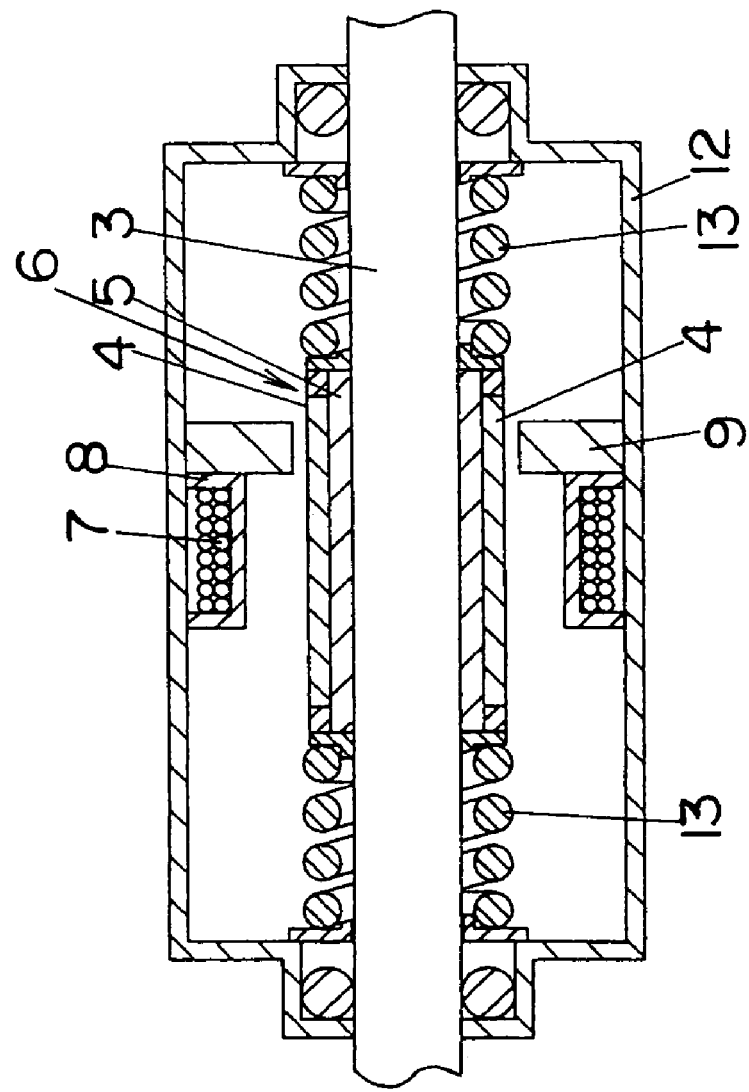
FIGS. 13A and 13B are respectively a sectional side view and a sectional rear view showing another modified example of the rolling driving actuator in accordance with the embodiment of the present invention.
Figure 13B:
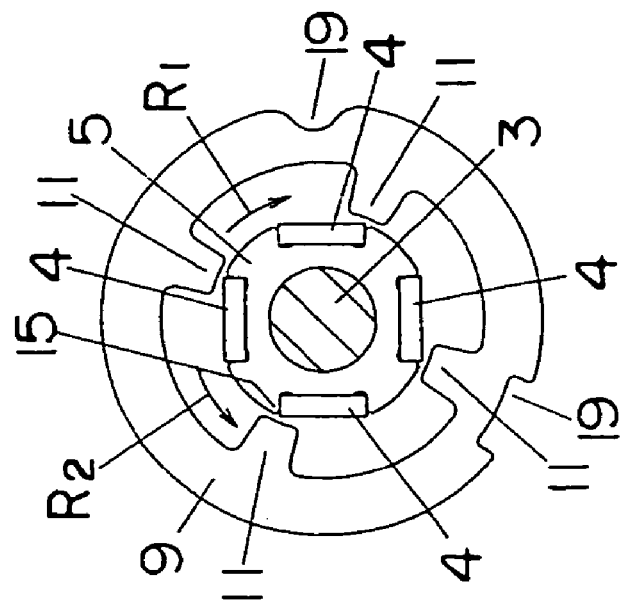

In the modified example shown in FIGS. 12A and 12B, in an initial state where no current is supplied to the coil 7, the magnetic poles 11 of the stationary yoke 9 are positioned to face the outer faces 4a of the flat plate shaped permanent magnets 4. And, in the modified example shown in FIGS. 13A and 13B, in the initial state where no current is supplied to the coil 7, the magnetic poles 11 of the stationary yoke 9 are positioned to face vicinities 15 of boundary between the flat plate shaped permanent magnets and the outer faces 5a of the yoke 5. In both cases, the motion of the moving object 6 is the same as the above description.

In the modified example shown in FIGS. 12A and 12B, when the yoke 5 is press-fitted to and fixed on the shaft 3, by press-fitting the yoke 5 in a manner so that the flat face portion of substantially D-shaped section of the rear end portion 3a of the shaft 3 becomes substantially parallel to the flat bottom face 25a of the substantially U-shaped groove 25 of the yoke 5, it has an advantageous merit that the proper assembling angle of the yoke 5 with respect to the shaft 3 can easily be decided. On the other hand, in the modified example shown in FIGS. 13A and 13B, by displacing the positions of the magnetic poles 11 of the yoke 9 from the flat plate shaped permanent magnets 4 similar to the case described with reference to FIGS. 5A to 5C, the initial driving force of the moving object 6 can be increased, so that it has an advantageous merit that the rolling driving can be started smoothly.

In the rolling driving actuator 2 in accordance with the present invention, the vibration system of the rolling driving is constituted by the moving object 6 rotatively driven around the axis of the shaft 3, and the spring members 13a, 13b and 13c supporting the moving object 6 around the axis of the shaft 3. A relationship between frequency and amplitude of the moving object 6 when a voltage of alternating current supplied to the coil 7 is set to be constant, and a relationship between the frequency and current at that time in such a rolling driving actuator in accordance with this embodiment are described with reference to a graph shown in FIG. 14.

Figure 14:
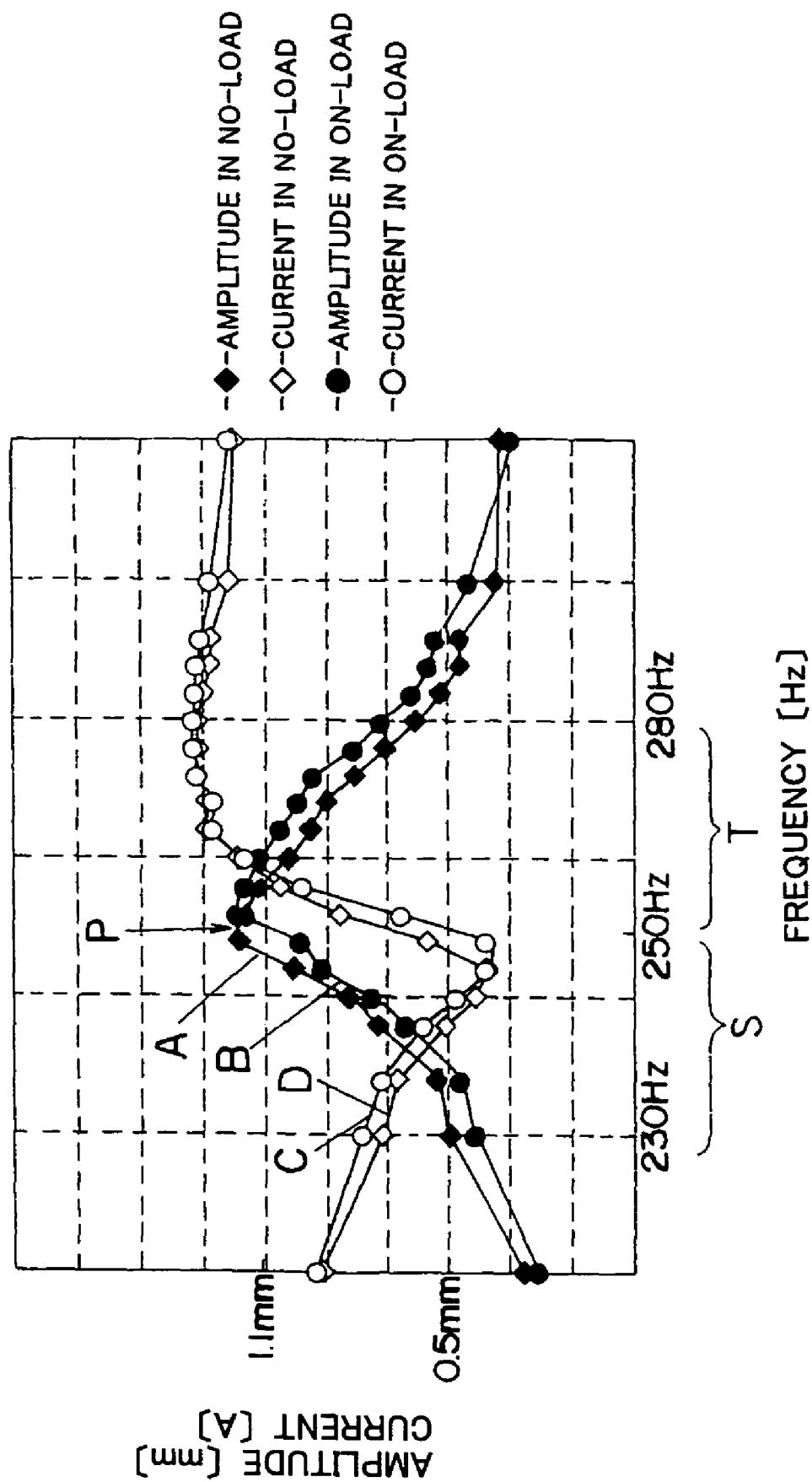
FIG. 14 is a graph showing a relation between frequency of alternating current and amplitude of the moving object when voltage is made to be constant in the rolling driving actuator and a relation between the frequency and current at that time.

In FIG. 14, curves A and B respectively show the relationship between frequency and amplitude of the moving object 6 when the voltage is set to be constant, and curves C and D respectively show the relationship between the frequency and current. In FIG. 14, a mark ♦ designates amplitude in no-load, a mark ● designates amplitude in on-load, a mark ◊ designates current value in no-load, and a mark ○ designates current value in no-load, respectively.

As mentioned before, the oscillation quantity (amplitude quantity) of the moving object 6 can be increased by supplying the alternating current having a frequency near to the resonance vibration frequency (shown by point P in FIG. 14) defined by the spring constant of the spring members 13a, 13b and 13c and the mass of the moving object 6 to the coil 7. For example, in the vicinity of frequency 250 Hz, the amplitude of the moving object 6 shows the maximum value 1.1 mm. In the region S of the frequency equal to or larger than 230 Hz and equal to or smaller than 250 Hz and in the region T equal to or larger than 250 Hz and equal to or smaller than 280 Hz, the amplitude shows a value equal to or larger than 0.5 mm, respectively.

When the frequency of the alternating current flowing to the coil 7 is set in these regions, it is possible to enlarge the oscillation quantity (amplitude quantity) of the moving object 6 with utilizing the spring members 13a, 13b and 13c. Hereupon, in the vicinity of the resonance vibration frequency, and in a region of frequency higher than the resonance vibration frequency and in a region of frequency lower than the resonance vibration frequency, amplitude similar to this can be obtained. When the moving object 6 is performed the rolling driving by setting the frequency lower than the resonance vibration frequency (when the frequency is set in the region S), it is possible to perform the rolling driving with the aimed amplitude by small current. Especially, when a power supply of the rolling driving actuator 2 is a battery, it is possible to make the operation life of the battery longer. On the other hand, when the frequency is set to be higher than the resonance vibration frequency (when the frequency is set in the region T), although the current becomes larger, it is possible to perform the rolling driving with the aimed amplitude so as to take a large output power.

The above-mentioned rolling driving actuator can be used as various kinds of driving force. As an example, a configuration of a power toothbrush comprising the above-mentioned rolling driving actuator is shown in FIG. 15.

The power toothbrush 1 comprises a tubular shaped slender housing 22, a rolling driving actuator 2 shown in above FIG. 1 provided in front side in the housing 22 in longitudinal direction, a battery (secondary battery) 21 provided in rear side in the housing 22 in the longitudinal direction, a control circuit unit 32, an electric switch 33 provided on an outer periphery portion of the housing 22, and so on. An end portion of the shaft 3 of the rolling driving actuator 2 is protruded outward from a front end face of the housing 22.

Figure 15:
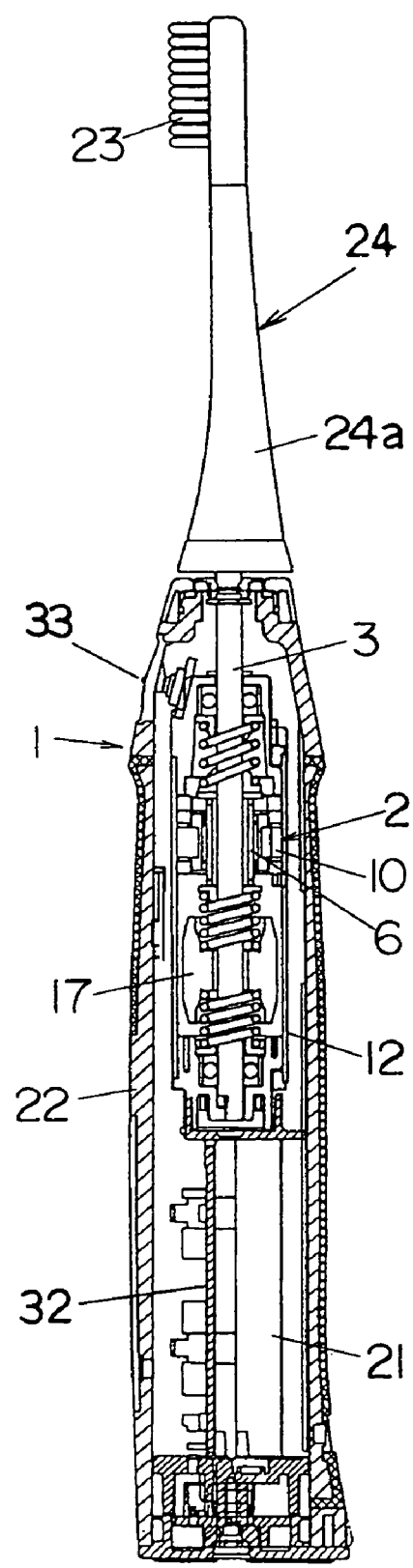
FIG. 15 is a sectional view showing a configuration of a power toothbrush using the rolling driving actuator in accordance with an embodiment of the present invention.
Figure 16:
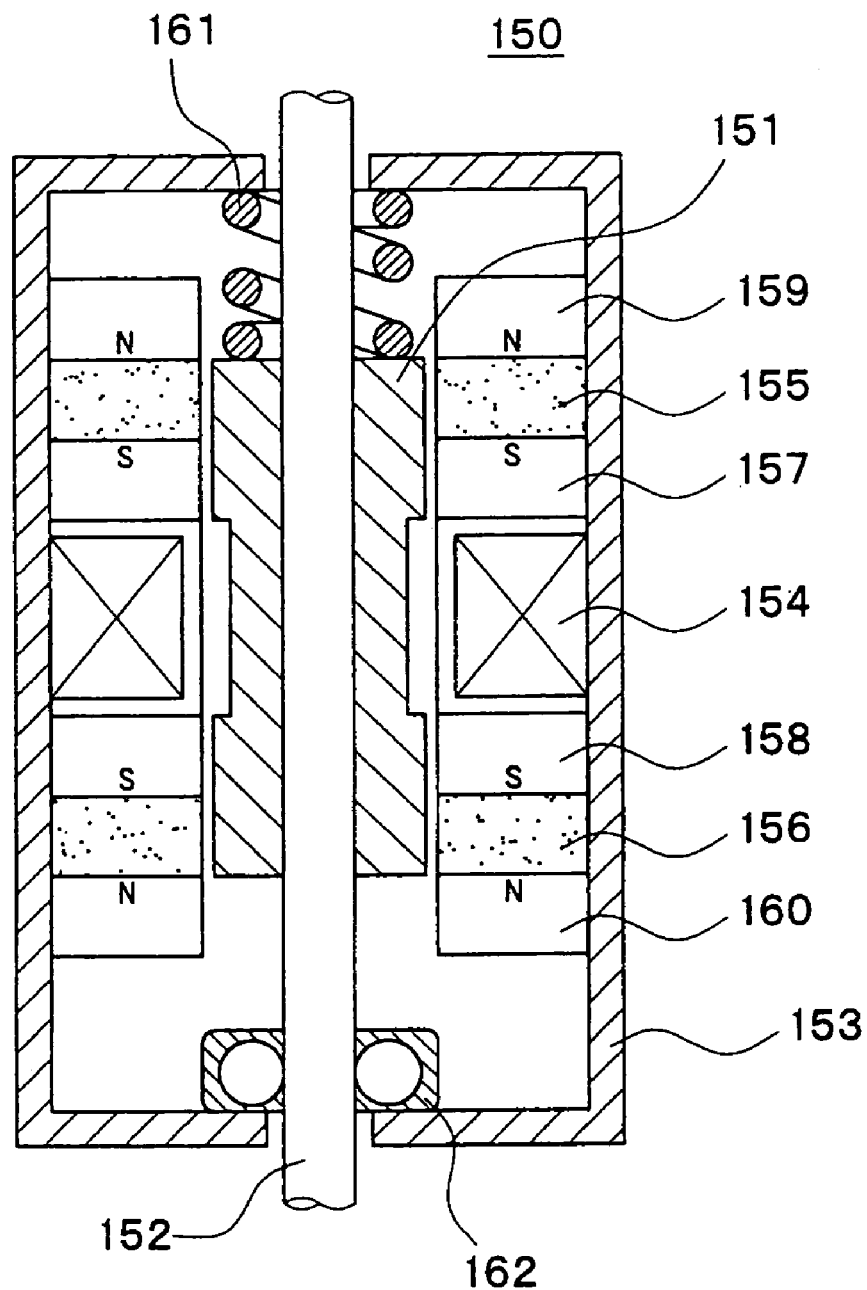
FIG. 16 is a sectional view showing a configuration of a conventional oscillation type linear actuator (reference example).

In the example shown in FIG. 15, since a brush body 24 is a type that a brush portion 23 at a front end thereof is implanted in a direction substantially perpendicular to longitudinal direction of the brush body 24, it is attached on the shaft 3 in a manner so that a rear end portion of a handle portion 24a of the brush body 24 is detachably attached on an end of the shaft 3, and not rotatable around the axis of the shaft 3. As shown in FIG. 1 and FIG. 2, since a vicinity of the front end of the shaft 3 is formed to have a substantially D-shaped section, by forming a fitting hole having a substantially D-shaped section, which is to be fitted to the front end portion of the shaft 3, on the handle portion 24a of the brush body 24, it is possible to restrict the brush body 24 not to rotate around the axis of the shaft 3. As a result, a positional relationship between the protruding direction of the brush portion 23 of the brush body 24 and the electric switch 33 provided on the housing 22 can be made constant, so that operability as the power toothbrush may not be failed.

When the electric switch 33 of the power toothbrushes 1 which is configured as above is operated to supply a current to the coil 7 of the rolling driving actuator 2, the shaft 3 can be performed the rolling driving around the axis thereof. Thereby, the brush body 24 attached on the shaft 3 is performed the rolling driving around the axis, so that brushing of teeth can be performed by driving the brush portion 23 reciprocally and linearly.

As mentioned above, according to the rolling driving actuator in accordance with this embodiment, it is configured that the permanent magnets 4 are formed to be flat plate shape and fitted to the grooves 25 formed on the yoke 5, so that the volume of each permanent magnet 4 becomes smaller, and manufacturing process of the permanent magnet 4 and assembling process of the moving object 6 are simplified. As a result, the costs of the rolling driving actuator and the power toothbrush using the same can be reduced.

In addition, the rolling driving actuator 2 in accordance with the present invention is not limited to be used as a driving source of the power toothbrush 1, but it is widely applicable as a driving source of a power shaver and other equipment.

This application is based on Japanese patent application 2003-139572 filed in Japan, the contents of which are hereby incorporated by references of the specification and drawings of the above patent application.

Although the present invention has been fully described by way of example with reference to the accompanying drawings, it is to be understood that various changes and modifications will be apparent to those skilled in the art. Therefore, unless otherwise such changes and modifications depart from the scope of the present invention, they should be construed as being included therein.

INDUSTRIAL APPLICABILITY

As mentioned above, in the rolling driving actuator of the present invention, it is configured that the flat plate shaped permanent magnet is attached to the groove formed on the yoke, so that the volume of the permanent magnet becomes smaller, and thereby the cost of the permanent magnet in material can be reduced in comparison with the conventional case that the tubular shaped permanent magnets is disposed on the inner face of the shielding case. Furthermore, the flat plate shaped permanent magnet magnetized in thickness direction is attached by fitting in the groove of the yoke, so that the manufacturing process of the permanent magnet and the assembling process of the moving object become simple, thereby, the cost of manufacturing the permanent magnet and the cost of assembling the moving object can be reduced. Still furthermore, the polarities of the outer face of the flat plate shaped permanent magnet and the outer face of the yoke becomes opposite to each other, so that the magnetic flux by the permanent magnet can easily be passed through the yoke, and thereby the magnetic flux by the permanent magnet can be utilized effectively. As a result, the rolling driving actuator, which can be miniaturized, light-weighted and is easily assembled, can be provided in low cost.

Furthermore, according to the power toothbrush in accordance with the present invention, the low cost rolling driving actuator, which can be miniaturized, light-weighted and is easily assembled, is used as mentioned above, the miniaturization, light-weighted, improvement of assemble workability, and reduction of the cost of the power toothbrush can be realized.

The invention claimed is:

1. A rolling driving actuator comprising:
   a moving object having a shaft pivoted to be able to rotate around an axis thereof, a yoke fixed on the shaft and flat plate shaped permanent magnets attached to adjoin the yoke around the axis of the shaft and magnetized in thickness direction thereof; and
   a tubular shaped stator having a coil wound around the axis of the shaft to enclose the moving object, and stationary yokes made of a magnetic material and disposed to face an outermost peripheral portion of the yoke and the permanent magnet with a predetermined clearance in a direction perpendicular to the axis of the shaft; and wherein each permanent magnet is fixed on the yoke in the same orientation so that all outer faces of the permanent magnets have the same polarity; and the moving object being driven in rolling driving in a predetermined angle region around the axis of the shaft by supplying alternating current to the coil.

2. The rolling driving actuator in accordance with claim 1 characterized by that the flat plate shaped permanent magnets are provided at more than two positions around the axis of the shaft and attached so that and polarities of respective of the flat plate shaped permanent magnets become the same.

3. The rolling driving actuator in accordance with claim 1 characterized by that the yoke is a substantially tubular shaped body press-fined to and fixed on the shaft, and has at least one groove parallel to the axial direction of the shaft on its outer face, to which the permanent magnet is fitted.

4. The rolling driving actuator in accordance with claim 1 characterized by further comprising a spring member for restricting rotation angle of the moving object in a predetermined region.

5. The rolling driving actuator in accordance with claim 4 characterized by further comprising a rotation restricting structure for mechanically stopping the rotation of the moving member when a force for rotating the moving object around the axis of the shaft more than a permissible region is applied from outside.

6. The rolling driving actuator in accordance with claim 1 characterized by that the stationary yokes are provided on both side of a bobbin around which the coil is wound in the axial direction of the shaft, and positions of magnetic poles of one stationary yoke are not coincided with positions of magnetic poles of the other stationary yoke around the axis of the shaft.

7. The rolling driving actuator in accordance with claim 6 characterized by that the magnetic poles provided on at least one stationary yoke of the stator are positioned to face contacting points of the flat plate shaped permanent magnet and the yoke of the moving object in an initial state where no current is supplied to the coil.

8. The rolling, driving actuator in accordance with claim 6 characterized by that a stationary yoke positioning portion for positioning the stationary yoke with respect to the bobbin around the axis of the shaft is provided on an end face of the bobbin in the axial direction of the shaft.

9. The rolling driving actuator in accordance with claim 1 characterized by that spring members for rotatably supporting the moving object around the axis of the shaft, and a vibrational absorption spindle supported in the axial direction and around the axis of the shaft by the spring members are further comprised;

the moving object and the spring members constitute a vibration system of the rolling driving;

a position of center of gravity of the vibrational absorption spindle is disposed on the axis of the shaft; and when the moving object is rotatively driven around the axis of the shaft, the vibrational absorption spindle is rotatively driven in opposite phase around the axis of the shaft.

10. The rolling driving actuator in accordance with claim 9 characterized by that a gap is provided between the vibrational absorption spindle and the moving object in a direction perpendicular to the axis of the shaft.

11. The rolling driving actuator in accordance with claim 9 characterized by that moment of inertia of the vibrational absorption spindle is set to be larger than moment of inertia of the moving object when the moving object is rotatively driven.

12. The rolling driving actuator in accordance with claim 1 characterized by that spring members for rotatably supporting the moving object around the axis of the shaft are further comprised;

the moving object and the spring members constitute a vibration system of the rolling driving; and the moving object is driven in rolling driving by supplying an alternating current having a frequency equal to or near to a resonance vibration frequency of the vibration system to the coil.

13. The rolling driving actuator in accordance with claim 1 characterized by that spring members for rotatably supporting the moving object around the axis of the shaft are further comprised;

the moving object and the spring members constitute a vibration system of the rolling driving; and the moving object is driven in rolling driving by supplying an alternating current having a frequency near to and lower than a resonance vibration frequency of the vibration system to the coil.

14. The rolling driving actuator in accordance with claim 1 characterized by that spring members for rotatably supporting the moving object around the axis of the shaft are further comprised;

the moving object and the spring members constitute a vibration system of the rolling driving; and the moving object is driven in rolling driving by supplying an alternating current having a frequency near to and higher than a resonance vibration frequency of the vibration system to the coil.

15. The rolling driving actuator in accordance with claim 1 characterized by that a shielding case of a substantially tubular shape that the stator is fixed on an inner peripheral face thereof is further comprised;

an engaging portion of a convex or concave shape is provided on an outer peripheral face of the stationary yoke parallel to the axis of the shaft; and a concave or convex shaped rotation restricting portion to be engaged with the engaging portion of the stationary yoke for restricting rotation of the stationary yoke around the axis of the shaft is provided on an inner peripheral face of the shielding case.

16. In a power toothbrush comprising: a brush body that brush is implanted at a front end thereof; a rolling driving actuator for rolling driving the brush body in a predetermined direction; an electric power supply for supplying electric power to the rolling driving actuator; and a driving circuit for supplying driving current to the rolling driving actuator; characterized by that the rolling driving actuator comprises:

a moving object having a shaft pivoted to be able to rotate around an axis thereof, a yoke fixed on the shaft and flat plate shaped permanent magnets attached to adjoin the yoke around the axis of the shaft and magnetized in thickness direction thereof; and a tubular shaped stator having a coil wound around the axis of the shaft to enclose the moving object, and stationary yokes made of a magnetic material and disposed to face an outermost peripheral portion of the yoke and the permanent magnet with a predetermined clearance in a direction perpendicular to the axis of the shaft; and wherein each permanent magnet is fixed on the yoke in the same orientation so that all outer faces of the permanent magnets have the same polarity; and the moving object is driven in rolling driving in a predetermined angle region around the axis of the shaft by supplying alternating current to the coil.

* * * * *